US011833357B2

(12) United States Patent
Shah et al.

(10) Patent No.: US 11,833,357 B2
(45) Date of Patent: *Dec. 5, 2023

(54) PAIRING OF EXTERNAL COMMUNICATION DEVICES WITH AN IMPLANTABLE MEDICAL DEVICE VIA A PATIENT REMOTE CONTROLLER

(71) Applicant: Boston Scientific Neuromodulation Corporation, Valencia, CA (US)

(72) Inventors: Chirag Shah, Valencia, CA (US); Peter Yoo, Burbank, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/068,971

(22) Filed: Dec. 20, 2022

(65) Prior Publication Data

US 2023/0117981 A1 Apr. 20, 2023

Related U.S. Application Data

(63) Continuation of application No. 17/447,384, filed on Sep. 10, 2021, now Pat. No. 11,559,693.
(Continued)

(51) Int. Cl.
*H04W 76/10* (2018.01)
*H04B 3/54* (2006.01)
(Continued)

(52) U.S. Cl.
CPC ..... *A61N 1/37223* (2013.01); *A61N 1/37247* (2013.01); *H04W 76/14* (2018.02)

(58) Field of Classification Search
CPC ............ A61N 1/37223; A61N 1/37247; A61N 1/36062; A61N 1/37252; A61N 1/37211;
(Continued)

(56) References Cited

U.S. PATENT DOCUMENTS 6,516,227 B1 2/2003 Meadows et al.
7,242,981 B2 7/2007 Ginggen
(Continued)

FOREIGN PATENT DOCUMENTS

EP 3711816 9/2020
WO 2021/046120 3/2021

OTHER PUBLICATIONS

Boston Scientific Corp., "Vercise™ DBS Remote Control 4: Directions for Use" (2020; downloaded from Internet Sep. 14, 2020).
(Continued)

*Primary Examiner* — Andrew Wendell
(74) *Attorney, Agent, or Firm* — Lewis & Reese, PLLC

(57) ABSTRACT

Techniques for pairing an external device such as a clinician programmer (CP) to an implantable medical device (IMD) are disclosed, which involve use of a remote controller (RC) paired to the IMD. The RC is placed into a CP pairing mode, which acts differently depending on the type of IMD paired to the RC. If the IMD is RF based, the CP pairing mode places the IMD in a pairing mode, thus allowing the CP to connect directly with the IMD via a RF telemetry protocol. If the IMD is magnetic-induction based, the CP pairing mode causes the RC to advertise its presence to the CP, allowing the CP to connect to the RC via the RF telemetry protocol. Because the RC is also paired with the IMD via a magnetic induction telemetry protocol, the RC acts as a passthrough device to allow communications between the CP and the IMD.

20 Claims, 12 Drawing Sheets

Related U.S. Application Data

(60) Provisional application No. 63/085,872, filed on Sep. 30, 2020.

(51) Int. Cl.
  *A61N 1/372* (2006.01)
  *H04W 76/14* (2018.01)

(58) Field of Classification Search
  CPC . H04W 36/0011; H04W 76/14; H04W 76/10; H04W 4/80; H04B 3/544; H04B 5/0031
  See application file for complete search history.

(56) References Cited

U.S. PATENT DOCUMENTS

| | | |
|---|---|---|
| 7,672,726 B2 | 3/2010 | Ginggen |
| 7,996,079 B2 | 8/2011 | Armstrong |
| 8,014,867 B2 | 9/2011 | Cooke et al. |
| 8,090,445 B2 | 1/2012 | Ginggen |
| 8,131,377 B2 | 3/2012 | Shi et al. |
| 8,150,516 B2 | 4/2012 | Levine et al. |
| 8,543,207 B2 | 9/2013 | Cooke et al. |
| 8,672,874 B2 | 3/2014 | Strickland et al. |
| 8,838,254 B2 | 9/2014 | McClure et al. |
| 8,983,615 B2 | 3/2015 | Tahmasian et al. |
| 9,411,027 B2 | 8/2016 | Von Arx et al. |
| 9,446,252 B2 | 9/2016 | Benson |
| 9,463,322 B2 | 10/2016 | Wingeier et al. |
| 9,707,402 B2 | 7/2017 | Aghassian |
| 9,855,433 B2 | 1/2018 | Shahandeh et al. |
| 9,867,983 B2 | 1/2018 | Doerr |
| 9,894,691 B1 | 2/2018 | Hellman et al. |
| 9,913,990 B2 | 3/2018 | Ter-Petrosyan et al. |
| 10,286,209 B2 | 5/2019 | Yoon et al. |
| 10,525,252 B2 | 1/2020 | Feldman et al. |
| 10,589,090 B2 | 3/2020 | Feldman et al. |
| 10,716,937 B2 | 7/2020 | Feldman et al. |
| 11,252,229 B2 | 2/2022 | Kim |
| 11,559,693 B2 * | 1/2023 | Shah .................... H04W 76/14 |
| 2007/0055324 A1 | 3/2007 | Thompson et al. |
| 2007/0191914 A1 | 8/2007 | Stessman |
| 2008/0319497 A1 | 12/2008 | Griffith et al. |
| 2012/0095529 A1 | 4/2012 | Parramon et al. |
| 2012/0215285 A1 | 8/2012 | Tahmasian et al. |
| 2013/0211266 A1 | 8/2013 | Sachanandani et al. |
| 2014/0273824 A1 | 9/2014 | Fenner et al. |
| 2014/0304773 A1 | 10/2014 | Woods et al. |
| 2015/0080982 A1 | 3/2015 | Funderburk |
| 2015/0231402 A1 | 8/2015 | Aghassian |
| 2015/0360038 A1 | 12/2015 | Zottola et al. |
| 2016/0184591 A1 | 6/2016 | Feldman et al. |
| 2017/0178493 A1 | 6/2017 | You et al. |
| 2017/0312530 A1 | 11/2017 | Schilling et al. |
| 2018/0021589 A1 | 1/2018 | Wu et al. |
| 2018/0071513 A1 | 3/2018 | Weiss et al. |
| 2018/0071520 A1 | 3/2018 | Weerakoon et al. |
| 2018/0140831 A1 | 5/2018 | Feldman et al. |
| 2019/0344087 A1 | 11/2019 | Ter-Petrosyan et al. |
| 2020/0001091 A1 | 1/2020 | Marnfeldt |
| 2020/0367055 A1 | 11/2020 | Caruso et al. |
| 2021/0022194 A1 | 1/2021 | Taylor et al. |

OTHER PUBLICATIONS

Boston Scientific Corp., "Vercise™ Neural Navigator 4 Programming Manual: Directions for Use" (2020; downloaded from Internet Sep. 14, 2020).

Boston Scientific Corp., "ImageReady™ MRI Guidelines for Boston Scientific Deep Brain Stimulation Systems" (2020; downloaded from Internet Sep. 14, 2020).

Boston Scientific Corp., Vercise™ DBS Remote Control 4 Handbook (2020).

Cypress Semiconductor Corp., "PSoC Creator Component Datasheet: Bluetooth Low Energy (BLE) 1.20," p. 34 (2015).

Recommendation ITU-R RS 1346: Sharing Between the Meteorological Aids Service and Medical Implant Communication Systems (MICS) Operating in the Mobile Service in the Frequency Band 401-406 MHZ (1998).

Texas Instruments, Inc., data sheet for "CC2640R2F SimpleLink™ Bluetooth® 5.1 Low Energy Wireless MCU" (Jan. 2020).

Invitation to Pay Additional Fees regarding corresponding PCT Application No. PCT/US2021/071427, dated Jan. 10, 2022.

International Search Report and Written Opinion regarding corresponding PCT Application No. PCT/US2021/071427, dated Mar. 4, 2022.

* cited by examiner

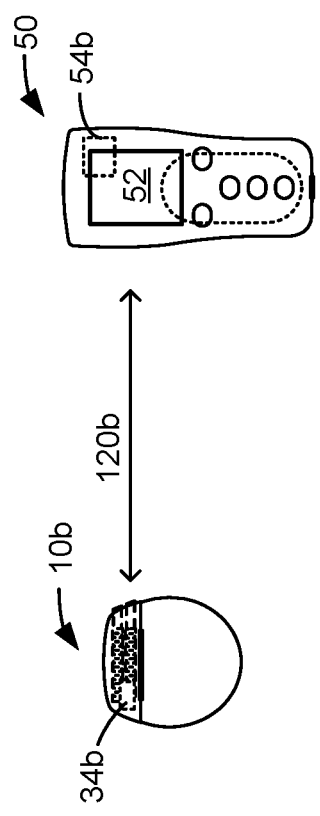
*Figure 4A*
*Figure 4B*
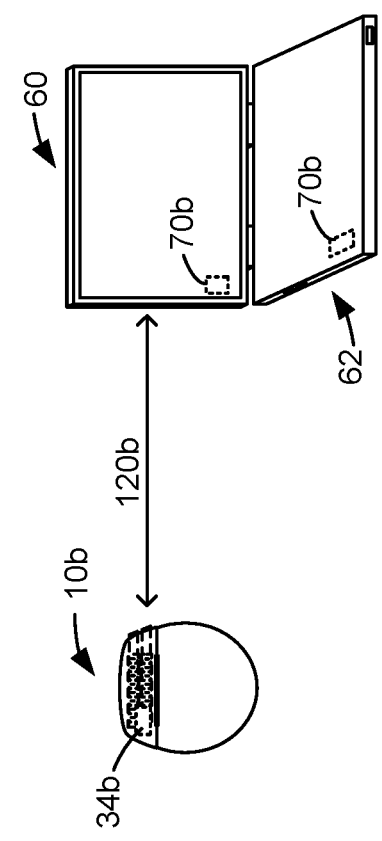
*Figure 4C*
*Figure 4D*

CP pairing mode—RF IPG 10b:

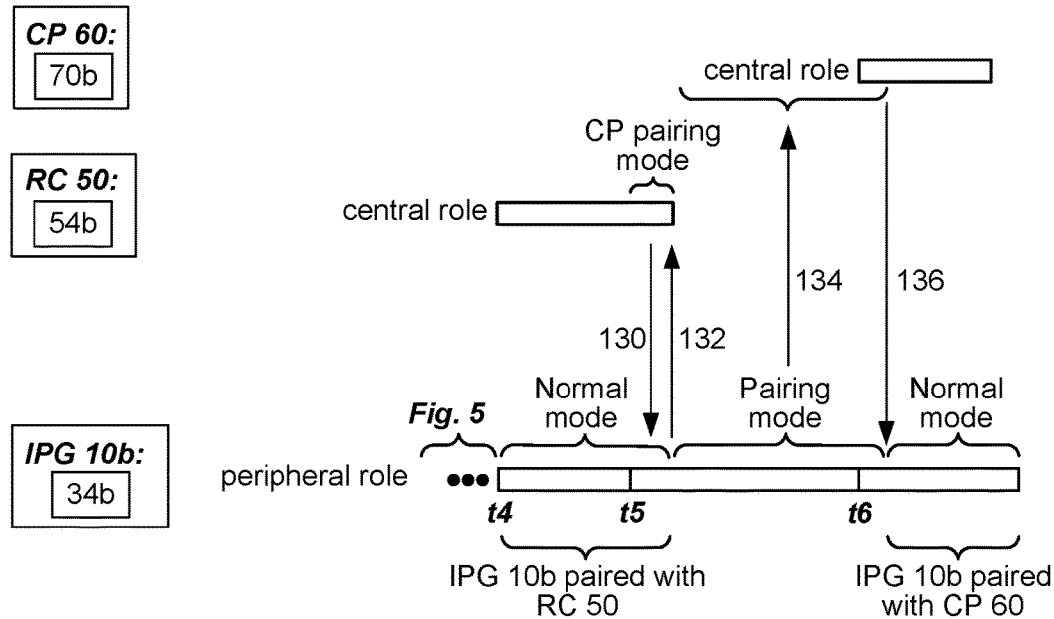

| t4: |
|---|
| - RC 50 paired with IPG 10b via RF antennas 54b and 34b; RC in central role<br>- IPG 10b in normal mode; provide stimulation; telemetry enabled with RC 50 |

| t5: |
|---|
| - Select CP pairing mode at RC 50 (Fig. 6B)<br>  • Select option on GUI, or<br>  • Display lock screen. While lock screen is displayed, press and hold programming button 55<br>- RC 50 recognizes it is currently paired with a RF IPG 10b (memory 116, Fig. 3)<br>- RC 50 sends CP pairing mode command 130 to IPG 10b<br>- IPG 10b receives CP pairing mode command 130, and operates in peripheral role; IPG 10b sends "CP mode ACK" 132 to RC 50<br>- IPG enters pairing mode; IPG periodically broadcasts pairing data 134 during transmission windows<br>- IPG DOES NOT ENTER RESET; stimulation continues<br>- In response to CP mode ACK 132, RC 50 disconnects from IPG 10b; display message on RC 50 that IPG 10b is ready for connection at the CP 60 (Fig. 6C) |

| t6: |
|---|
| - Select IPG pairing at CP 60; scan for devices (Fig. 6D)<br>- CP 60 receives pairing data 134 from IPG 10b; user transmits connection request 136 to IPG 10b using CP 60<br>  • authentication may be required if IPG/CP 60 not previously paired<br>- CP 60 paired with IPG 10b via RF antennas 70b and 34b; IPG 10b exits pairing mode; automatically enters normal mode; stimulation continues; telemetry enabled with CP 60<br>- CP 60 can display information about connection with IPG 10b (Fig. 6E) |

*Figure 6A*

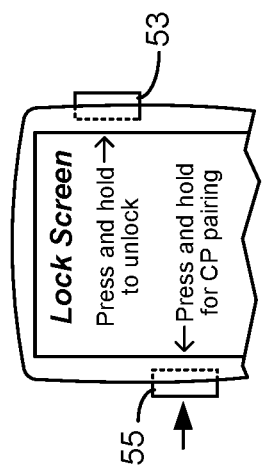
*Figure 6B*
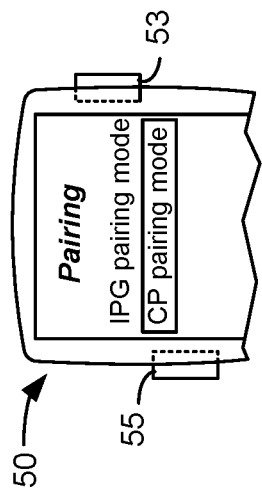
*Figure 6C*
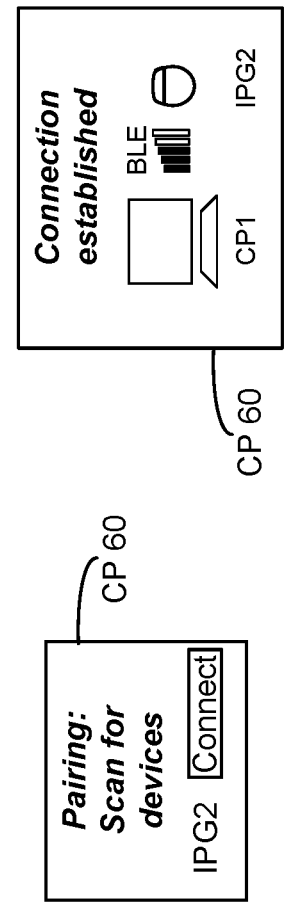
*Figure 6D*
*Figure 6E*
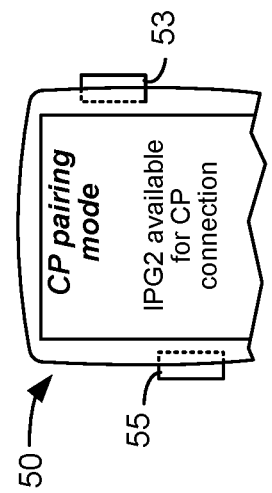

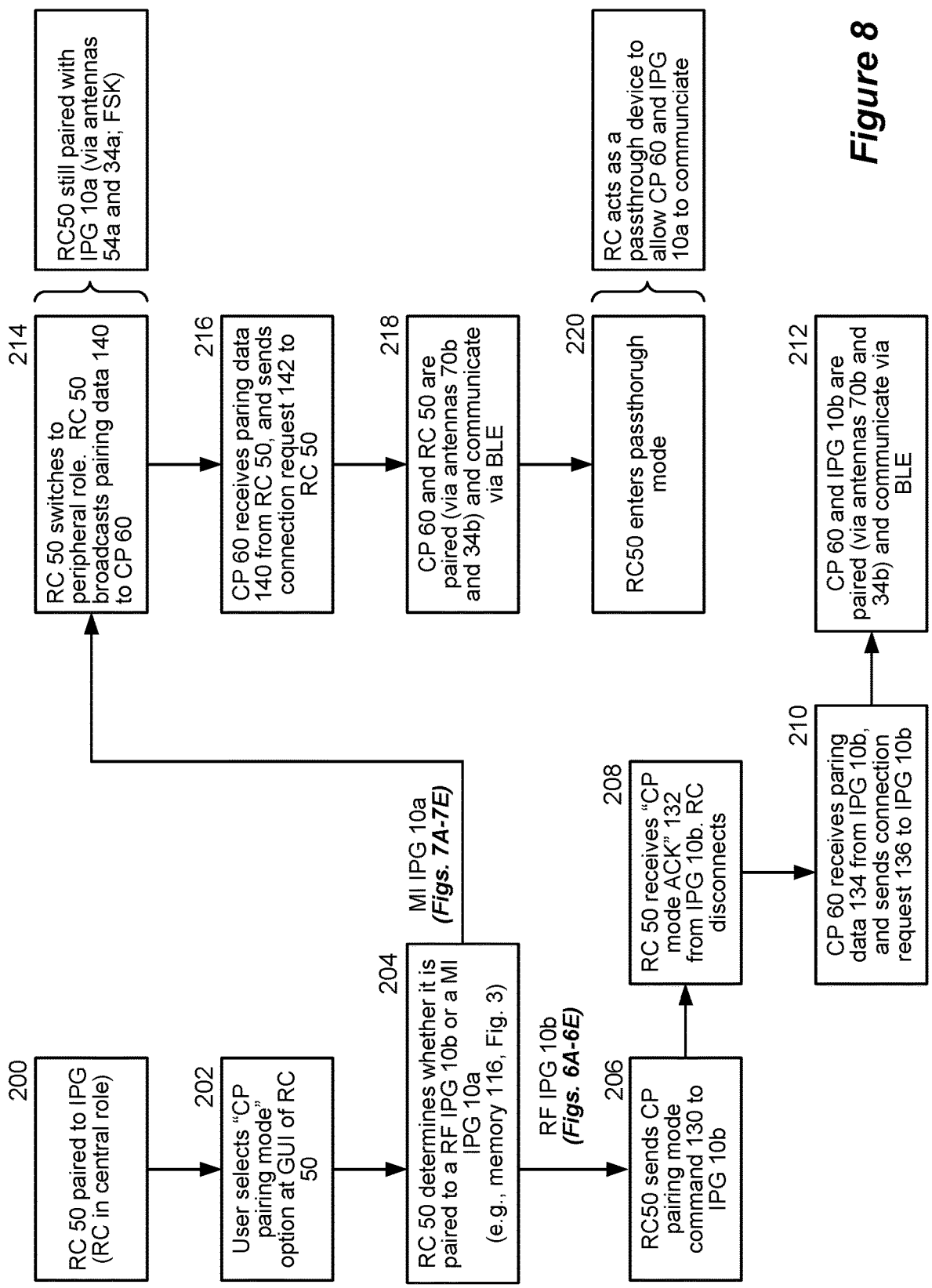

PAIRING OF EXTERNAL COMMUNICATION DEVICES WITH AN IMPLANTABLE MEDICAL DEVICE VIA A PATIENT REMOTE CONTROLLER

CROSS REFERENCE TO RELATED APPLICATIONS

This is continuation of U.S. patent application Ser. No. 17/447,384, filed Sep. 10, 2021, which is a non-provisional application of U.S. Provisional Patent Application Ser. No. 63/085,872, filed Sep. 30, 2020. These applications are incorporated by reference in their entireties, and priority is claimed to them.

FIELD OF THE INVENTION

This application deals with implantable medical device (IMDs) systems and manners in which external devices can be paired for communications with an IMD.

INTRODUCTION

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Deep Brain Stimulation (DBS) or Spinal Cord Stimulation (SCS) system, such as that disclosed in U.S. Pat. No. 6,516,227 and U.S. Patent Application Publication 2016/0184591. However, the present invention may find applicability with any implantable neurostimulator device system.

A DBS or SCS system typically includes an Implantable Pulse Generator (IPG) 10 shown in FIG. 1. The IPG 10 includes a biocompatible device case 12 that holds the circuitry and a battery 14 for providing power for the IPG to function. The IPG 10 is coupled to tissue-stimulating electrodes 16 via one or more electrode leads that form an electrode array. For example, one or more percutaneous leads 18 can be used having electrodes 16 carried on a flexible body. In another example, a paddle lead 20 provides electrodes 16 positioned on one of its generally flat surfaces. Lead wires within the leads are coupled to the electrodes 16 and to proximal contacts 22 insertable into lead connectors 24 fixed in a header 26 on the IPG 10, which header can comprise an epoxy for example. Once inserted, the proximal contacts 22 connect to header contacts 28 within the lead connectors 24, which are in turn coupled by feedthrough pins 30 through a case feedthrough 32 to stimulation circuitry 36 within the case 12. The number and type of leads, and the number of electrodes on such leads, can vary depending on the application. The conductive case 12 can also comprise an electrode.

In a SCS application, as is useful to alleviate chronic back pain for example, the electrode lead(s) are typically implanted in the spinal column proximate to the dura in a patient's spinal cord, preferably spanning left and right of the patient's spinal column. The proximal contacts 22 are tunneled through the patient's tissue to a distant location such as the buttocks where the IPG case 12 is implanted, at which point they are coupled to the lead connectors 24. In a DBS application, as is useful in the treatment of tremor in Parkinson's disease for example, the IPG 10 is typically implanted under the patient's clavicle (collarbone). Percutaneous leads 18 are tunneled through and under the neck and the scalp where the electrodes 16 are implanted through holes drilled in the skull and positioned for example in the subthalamic nucleus (STN) and the pedunculopontine nucleus (PPN) in each brain hemisphere.

IPG 10 can also comprise functionally-similar devices that are not fully implantable in the patient, such as an External Trial Stimulator (ETS). An ETS has leads implantable in the patient but connected to a circuitry portion that is external to the patient. When an ETS is used, stimulation can be tried on a prospective implant patient without going so far as to implant the IPG's case 12. ETS devices are explained further in U.S. Published Patent Application 2020/0001091. For purpose of this disclosure, an IPG should be understood to include ETSs as well.

IPG 10 can include an antenna 34a allowing it to communicate bi-directionally with a number of external devices discussed subsequently. Antenna 34a as shown comprises a conductive coil within the case 12, although the coil antenna 34a can also appear in the header 26. When antenna 34a is configured as a coil, communication with external devices preferably occurs using near-field magnetic induction, using a communication scheme like Frequency Shift Keying (FSK) for example. See, e.g., U.S. Patent Application Publication 2015/0080982 (describing the use of FSK in magnetic-inductive implantable medical device telemetry). IPG 10 may also include a Radio-Frequency (RF) antenna 34b. In FIG. 1, RF antenna 34b is shown within the header 26, but it may also be within the case 12. RF antenna 34b may comprise a patch, slot, or wire, and may operate as a monopole or dipole. RF antenna 34b preferably communicates using far-field electromagnetic waves, and may operate in accordance with any number of known RF communication standards, such as Bluetooth, Zigbee, WiFi, MICS, and the like.

Stimulation in IPG 10 is typically provided by pulses, as described in the above-referenced '091 Publication. Pulses can be formed by stimulation circuitry 36 in the IPG, again as described in the '091 Publication. Stimulation circuitry 36 can comprise a part of, or can communicate with, the IPG's control circuitry 38. The control circuitry 38 can comprise a microcontroller, microprocessor, Field Programmable Grid Array, Programmable Logic Device, Digital Signal Processor or like devices. In one example, control circuitry 38 can comprise or include an MSP430 microcontroller device, manufactured by Texas Instruments, Inc. Control circuitry 38 may also be based on well-known ARM microcontroller technology. Control circuitry 38 may include a central processing unit capable of executing instructions, with such instructions stored in volatile or non-volatile memory within the control circuitry. Control circuitry 38 may also include, operate in conjunction with, or be embedded within, an Application Specific Integrated Circuit (ASIC), such as described in U.S. Patent Application Publications 2008/0319497, 2012/0095529, 2018/0071513, or 2018/0071520, which are incorporated herein by reference. The control circuitry 38 may comprise an integrated circuit with a monocrystalline substrate, or may comprise any number of such integrated circuits. Control circuitry 38 may also be included as part of a System-on-Chip (SoC) or a System-on-Module (SoM) which may incorporate memory devices and other digital interfaces.

IPG 10 may also include a magnetic field sensor 40, such as a Hall effect sensor. Magnetic field sensor 40 can also comprise other devices or circuits in the IPG, for example as taught in U.S. Pat. No. 10,589,090 and U.S. Patent Application Publication 2007/0191914. Use of the magnetic field sensor 40 in an IPG 10 is explained further below.

FIG. 2 shows various external devices that can wirelessly communicate with the IPG 10, including a patient hand-held remote controller (RC) 50 and a clinician programmer (CP) 60. Both of devices 50 and 60 can be used to wirelessly transmit information, such as a stimulation program, to the IPG 10—that is, to program stimulation circuitry 36 with a stimulation program to produce stimulation (e.g., pulses) with a desired amplitude and timing (e.g., pulse width and frequency). Both devices 50 and 60 may also be used to adjust one or more stimulation parameters of a stimulation program that the IPG 10 is currently executing, to update software in these devices, or to place the IPG into different operational modes as discussed further below. Devices 50 and 60 may also wirelessly receive information from the IPG 10, such as various status information, etc.

Clinician programmer (CP) 60 is described further in U.S. Patent Application Publication 2015/0360038, and can comprise a computing device 62, such as a desktop, laptop, notebook computer, tablet, mobile smart phone, or Personal Data Assistant (PDA)-type mobile computing device, etc. In FIG. 2, computing device 62 is shown as a laptop computer that includes typical computer user interface means such as a screen 64, a mouse, a keyboard, speakers, a stylus, a printer, etc., not all of which are shown for convenience. Also shown in FIG. 2 are accessory devices for the CP 60 that are usually specific to its operation as a stimulation controller, such as a communication "wand" 66 coupleable to suitable ports (e.g., USB ports 69) on the computing device 62.

The antenna used in the CP 60 to communicate with the IPG 10 can depend on the type of antennas included in the IPG. If the patient's IPG 10 includes a coil antenna 34*a*, wand 66 can likewise include a coil antenna 70*a* to establish near-field magnetic-induction communications at small distances. In this instance, the wand 66 may be affixed in close proximity to the patient, such as by placing the wand in a belt or holster wearable by the patient and proximate to the patient's IPG 10. If the IPG 10 includes an RF antenna 34*b*, the wand 66, the computing device 62, or both, can likewise include an RF antenna 70*b* to establish communication at larger distances.

To program stimulation programs or parameters for the IPG 10, or to otherwise control the IPG 10, the clinician interfaces with a clinician programmer graphical user interface (GUI) 72 provided on the display 64 of the computing device 72. As one skilled in the art understands, the GUI 72 can be rendered by execution of clinician programmer software 74 stored in the computing device 72, which software may be stored in the device's non-volatile memory 76. Execution of the clinician programmer software 74 in the computing device 62 can be facilitated by control circuitry 78 such as one or more microprocessors, microcomputers, FPGAs, DSPs, other digital logic structures, etc., which are capable of executing programs in a computing device, and which may comprise their own memories. For example, control circuitry 78 can comprise an i5 processor manufactured by Intel Corp, as described at https://www.intel.com/content/www/us/en/products/processors/core/i5-processors.html. Such control circuitry 78, in addition to executing the clinician programmer software 74 and rendering the GUI 72, can also enable communications via antennas 70*a* or 70*b* to communicate stimulation parameters chosen through the GUI 72 to the patient's IPG 10.

Remote controller (RC) 50 can be as described in U.S. Patent Application Publication 2015/0080982 for example, and may comprise a controller dedicated to work with the IPG 10. RC 50 may also comprise a general purpose mobile electronics device such as a mobile phone which has been programmed with a Medical Device Application (MDA) allowing it to work as a wireless controller for the IPG 10, as described in U.S. Patent Application Publication 2015/0231402. Like the CP 60, RC 50 includes a graphical user interface including a display 52 and means for entering commands or selections, such as buttons 56 or selectable graphical elements rendered on the display. The RC 50's graphical user interface also enables a patient to adjust stimulation parameters, although it may have limited functionality when compared to the more-powerful CP 60 described above. The RC 50 may also include a lock screen button 53 to unlock the display and otherwise power up the RC after it has gone into a power-down mode, and a programming button 55 as explained further below.

The RC 50 can have one or more antennas capable of communicating with the IPG 10. For example, the RC 50 can have a near-field magnetic-induction coil antenna 54*a* capable of wirelessly communicating with the coil antenna 34*a* in the IPG 10. The RC 50 can also have a far-field RF antenna 54*b* capable of wirelessly communicating with the RF antenna 34*b* in the IPG 10. The RC 50 includes control circuitry 58 which may be similar to the control circuitry in the CP 60, and which includes memory for storing software and the like. The RC 50 typically has a battery (not shown) to provide operating power, and such battery is usually rechargeable (similar to a cell phone).

The IPG 10, RC 50, and CP 60, as well as communicating with each other, can communicate with a network 80. Network 80 can comprise a WiFi gateway and the Internet for example, and communication between the devices can occur using the network 80 as an intermediary. A server 81 can be connected to the network, which can for example be used to send stimulation programs or other useful information (e.g., software updates) to the various devices in the system.

FIG. 2 further shows a permanent bar magnet 90 in the communication system for the IPG 10. Use and function of the bar magnet 90 is described further below.

BRIEF DESCRIPTION OF THE DRAWINGS

FIGS. 4A-4D show further details regarding communication between the MI IPG and the RC or CP, and between the RF IPG and the RC or CP.

FIGS. 6A-6E show use of the RC to facilitate pairing an RF IPG to the CP, where the RC has determined that the RF IPG and CP can communicate directly.

FIG. 8 shows a flow chart of an algorithm whereby the RC facilitates pairing an IPG of an unknown type to the CP, with the RC determining the type of IPG and taking appropriate action to either cause the IPG and CP to communicate directly or through the RC as an intermediary.

DETAILED DESCRIPTION

Figure 3:
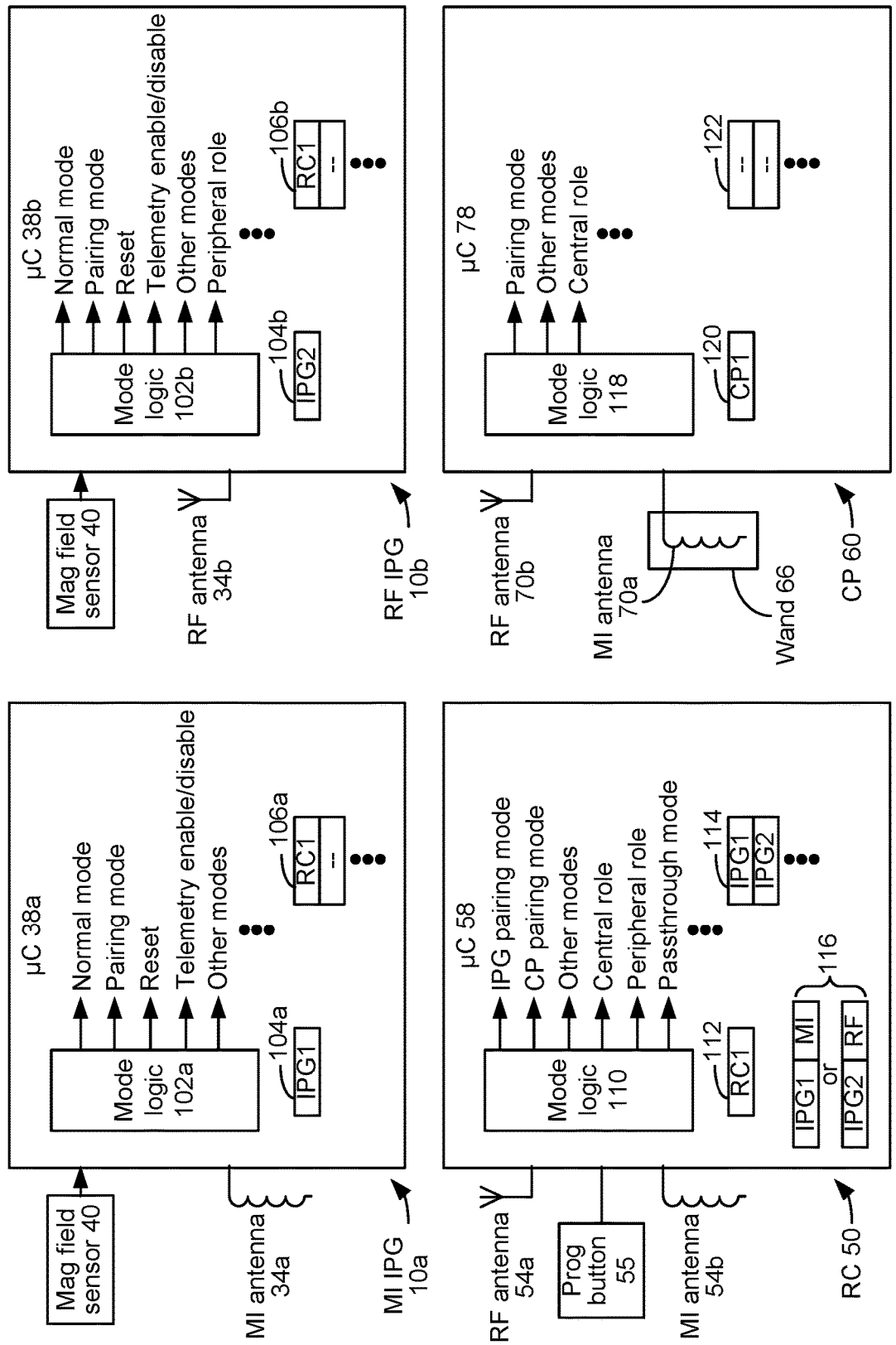
FIG. 3 shows further details of devices that are potentially implicated when used with the disclosed pairing techniques, including a magnetic induction (MI) IPG with a MI antenna, a Radio Frequency (RF) IPG with an RF antenna, and remote controller (RC), and a clinician programmer (CP).

FIG. 3 shows further details of devices that are potentially implicated when used with the disclosed techniques. Two different types of implants are shown, which differ in the type of antennas they have and the types of communications they support. IPG 10a includes a magnetic induction (MI) coil antenna 34a, which communicates with external devices via magnetic induction and using a communication scheme such as FSK, as described earlier. IPG 10b includes a Radio Frequency (RF) antenna 34b, which communicates with external devices via RF telemetry in accordance with an appropriate RF communication standard, such as Bluetooth, or Bluetooth Low Energy (BLE). BLE is assumed from this point forward as the relevant RF communication standard used in the system, although other far-field communication standards could be used as well. IPGs like 10a having MI antennas 34a are established in the art, while IPGs like 10b having RF antennas 34b are newer and are expected to eventually replace IPGs like IPG 10a in the marketplace.

FIG. 3 also includes a remote controller (RC) 50. In this example, the RC 50 includes both a MI antenna 54a that can be used to communicate with MI IPG 10a (via MI antenna 34a, using FSK for example), and an RF antenna 54b that can be used to communicate with RF IPG 10b (via RF antenna 34b, using BLE for example). FIG. 3 further includes a clinician programmer (CP) 60. As described earlier, the CP 60 can include one or more RF antennas 70b, which are typically integrated with the CP's computing device 62, but which may also be connected to the computing device. The CP 60 can use RF antenna 70b to communicate with RF IPG 10b (antenna 34b, BLE). The CP 60 further includes a communication wand 66, which includes a MI coil antenna 70a, which can be used to communicate with MI IPG 10a (antenna 34a, FSK). The CP 60 and RC 50 can also communicate with each other, and as most relevant here will communicate using BLE (via RF antennas 54b and 70b), although they could also communicate using magnetic induction (MI antennas 54a and 70a).

The control circuitry 38a, 38b, 58, and 78 of each of these devices 10a, 10b, 50, and 60 can include or communicate with memories 104a, 104b, 112, and 120 that store the devices' ID codes (IPG1, IPG2, RC1, CP1), and possibly other credentials or certificates that allow the device to communicate with other devices in the system. These ID codes can include or comprise serial numbers for the respective devices. The devices can also include memories 106a, 106b, 114, and 122 that store the ID codes (and other credentials and certificates) for devices which with they have previously been paired for communications. For example, it is assumed that RC 50 has previously been paired with IPG 10a and 10b, and thus stores the ID codes for these devices (IPG1, IPG2) in memory 114, along with other credentials or certificates to facilitate communicate with these devices in the future. Consistent with this, IPGs 10a and 10b also store the ID code for RC 50 (RC1) in their memories 106a and 106b. It is further assumed that CP 60 has not previously been paired with the RC 50 or either of IPGs 10a or 10b, and thus memory 122 is blank. Consistent with this, IPGs 10a and 10b and RC 50 do not store the ID code for CP 60 (CP1) in their memories 106a, 106b, or 114.

The control circuitries 38a, 38b, 58, and 78 of devices 10a, 10b, 50, and 60 can include mode logic circuitry 102a, 102b, 110, and 118 programmed to place the devices into different modes and under certain conditions as explained further below. For example, IPG 10a and 10b can operate in a normal mode, which comprises the basic mode in which the IPG is active and providing stimulation to the patient. Mode logic 102a and 102b can also cause IPGs 10a and 10b to operate in a pairing mode to allow these devices to be paired for communications with external devices such as RC 50 and CP 60. Mode logic 102a and 102b can also issue certain control signals which may be associated with one of more of these modes. For example, an IPG reset control signal may issue as explained further below, and telemetry can be enabled or disabled. Mode logic 102a and 102b may also place the IPGs into other various modes that are not relevant to discuss here. Mode logic 102a and 102b is responsive, at least, to the magnetic field sensor 40 in the IPG, and to commands that are received at the IPG's antennas 34a or 34b. Although not shown, one skilled will understand that the IPG would include demodulation circuitry to convert telemetry received at the antennas 34a or 34b into digital information understandable by the mode logic 102.

Mode logic 110 in the RC 50 is capable of placing the RC 50 in different pairing modes depending on which devices in the system the RC 50 is to be paired. For example, when the RC 50 is to be paired with one of the IPGs 10a or 10b, the RC 50 can operate in an IPG pairing mode. When the RC 50 is to be paired with the CP 60, the RC 50 can operate in an CP pairing mode. Mode logic 110 can be responsive to programming button 55, and this button can be used to place the RC in the CP pairing mode, as described further below. The RC can also operate in a passthrough mode, explained further below. Mode logic 118 in the CP 60 can place the CP into a pairing mode, which may allow the CP to be paired with the RC 50 or either of the IPGs 10a and 10b, as explained further below.

The control circuitry 58 in the RC 50 further includes a memory 116 to store information regarding the IPG with which the RC is currently paired, i.e., either MI IPG 10a (IPG 1) or RF IPG 10b. As described further below, the IPG to which the RC 50 is connected can affect operation of the RC 50 during the CP pairing mode.

Particularly as concerns RF communications via BLE, the mode logics 102b, 110, and 118 in the RF IPG 10b, the RC 50, and the CP 60 can operate in either a central role or a peripheral role. Operation in these roles can be dictated by the programming of the BLE chip sets used in these devices, which chip sets can comprise part of mode logics 102b, 110, and 118. As one skilled in the art will understand, upon start up, the mode logic in these devices will set the device to operate in one of these two roles. When acting in a peripheral role, the device is able to advertise its presence (provide pairing data) and waits for a central role device to connect to it. When acting in a central role, the device is able to scan for other peripheral devices to connect to upon receiving their advertisement data. After a central role and peripheral role device connect, they respectively operate as a server (master) and client (slave). In the disclosed system, IPG 10b preferably acts only in a peripheral role, and the CP 60 preferably only acts in a central role, but this could be varied in other implementations. By contrast, the mode logic 110 in the RC 50 can program the RC to operate in either a central or a peripheral role depending on the circumstances, as explained further below. Note that these roles can affect, and are related to, the various modes described, as explained further below. Note that operation in central or peripheral roles is not relevant to MI IPG 10a, as this device lacks BLE communication ability. Nevertheless, IPG 10a preferably generally operates consistently with a peripheral role in the system.

FIGS. 4A-4D shows details of communications between the different types of IPGs and the RC 50 or CP 60. In FIG. 4A, a MI IPG 10a communicates with the RC 50, and because the IPG has only a magnetic-induction coil antenna 34a, it communicates with RC 50's MI antenna 54a via MI communication link 120a (e.g., FSK). In FIG. 4B, a RF IPG 10b communicates with the RC 50, and because the IPG has only a RF antenna 34a, it communicates with RC 50's RF antenna 54b via RF communication link 120b (e.g., BLE). In FIG. 4C, a MI IPG 10a communicates with the CP 60, with its MI antenna 34a communicating with the MI antenna 70a in the wand 66 attached to the CP 60 via MI communication link 120a (e.g., FSK). In FIG. 4D, a RF IPG 10b communicates with the CP 60, with its RF antenna 34b communicating with the RF antenna 70b in or attached to the CP's computing device 62. Note that use of the wand is unnecessary in FIG. 4D. Because magnetic induction occurs at shorter distances, communication links 120a (FIGS. 4A & 4C) require the relevant devices to be relatively close to each other, such as no more than about 18 inches apart. By contrast, because RF telemetry can occur at longer distances, communication links 120b (FIGS. 4B & 4D) allow the relevant devices to be farther apart, such as up to 25 feet.

Figure 1:
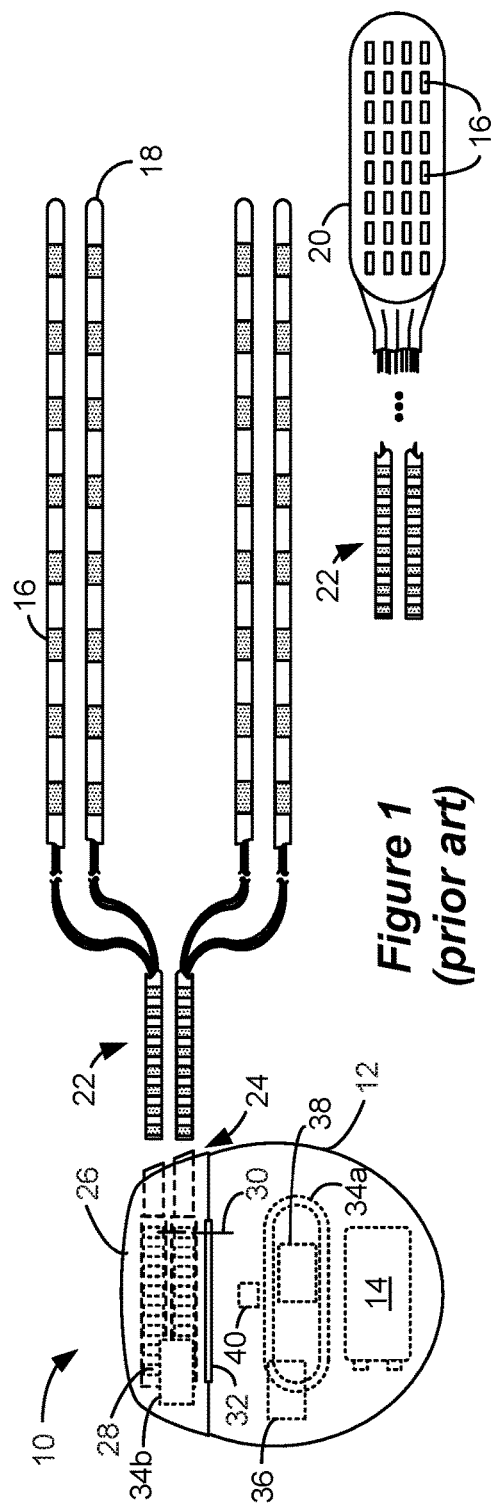
FIG. 1 shows an Implantable Pulse Generator (IPG), in accordance with the prior art.
Figure 2:
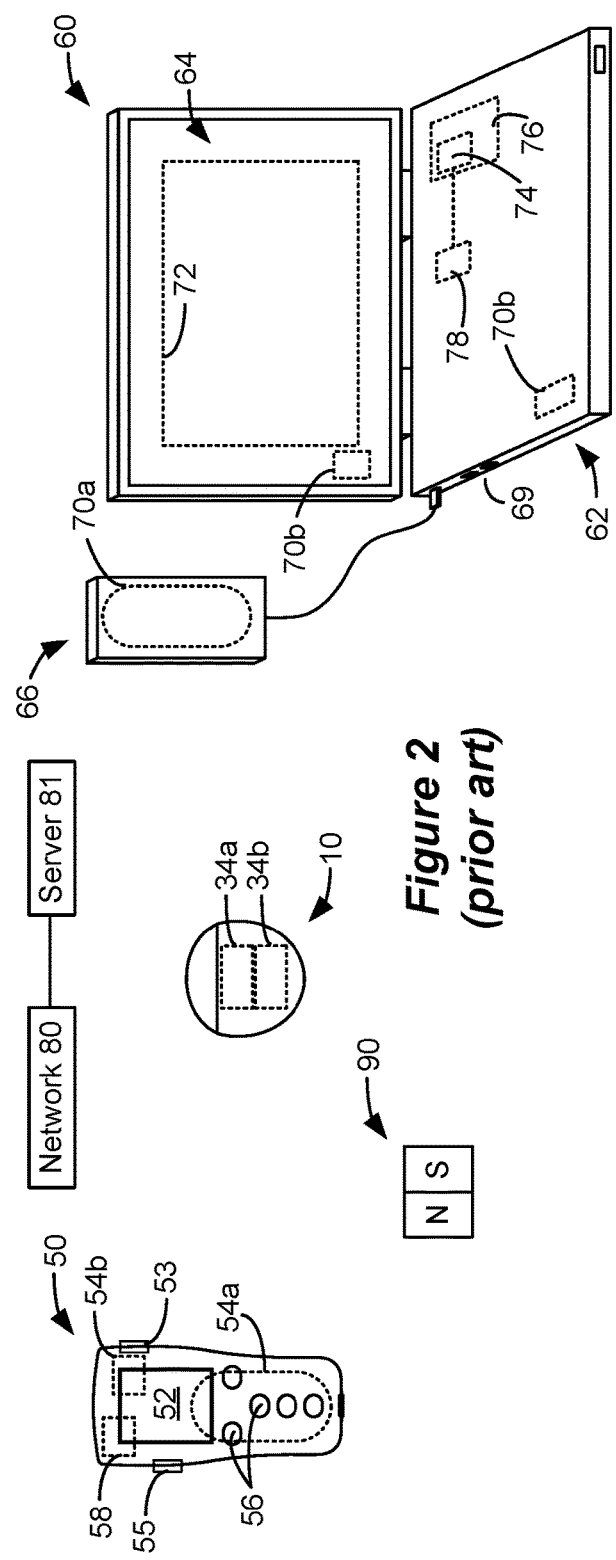
FIG. 2 shows various external devices capable of communicating with and programming stimulation in an IPG, in accordance with the prior art.
Figure 5:
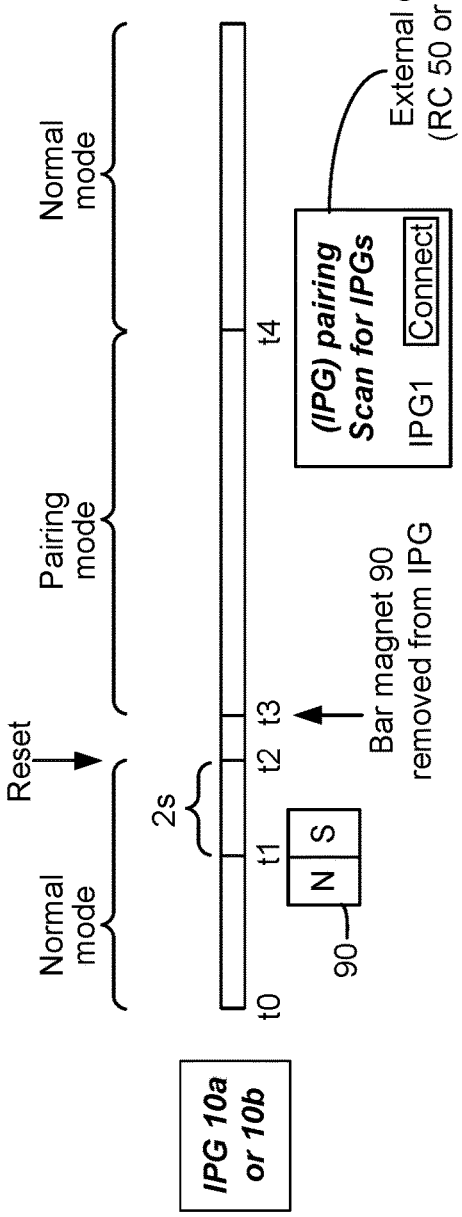
FIG. 5 shows use of a bar magnet to pair an IPG with an external device such as the RC or CP.

FIG. 5 shows how an external device—either RC 50 or CP 60—can be paired for communications with either of IPGs 10a or 10b. While pairing between these devices can occur in different ways, in this example, bar magnet 90 (FIG. 2) is used, which also resets the IPGs before placing the IPG into a pairing mode. It is assumed here that pairing occurs similarly in MI IPG 10a and RF IPG 10b, but it should be noted that these different types of IPGs can also involve the use of different pairing schemes. Note that the communication antennas involved when pairing in FIG. 5 will depend upon the device at issue, as explained with respect to FIGS. 4A-4D. For example, when an RF IPG 10b is being paired with the RC 50, this will involve the use of RF antennas 34b and 54b (FIG. 4B); when an MI IPG 10a is being paired with the CP 60, this will involve the use of MI antennas 34a and MI antenna 70b in the wand 66 (FIG. 4C), etc.

The pairing mode is discussed chronologically, and at t0 it is assumed that the IPG is operating in a normal mode. In the normal mode, the IPG is controlled (by mode logic 102a or 102b) to provide normal stimulation. Normal telemetry is also enabled in the normal mode, as are other IPG functions not relevant to mention here. When normal telemetry is enabled, the IPG can freely communicate with external devices with which the IPG 100 has already been paired, exchanging previously stored credentials or certificates as necessary. Preferably, to save power in the IPG, normal telemetry is enabled by periodically powering the antennas 34a or 34b in the IPG and any associated communication circuitry (e.g., modulation and demodulation circuitry) during short listening windows (e.g., 10 ms) which are issued at a period of about 1 second. How normal telemetry occurs with a paired external can depend on the type of connection to be established and the communication standard that governs that connection. For example, if Bluetooth or Bluetooth Low Energy (BLE) is used for the connection, the IPG 10b can listen for a broadcast from the external device during each of the listening windows. Upon receiving proper credentials from the external device (such as the external device's ID code), a communication session can be established, at which time the IPG can continuously power its antenna 34a or 34b and associated communication circuitry until the end of the communication session. Although not set forth in FIG. 5, the IPG can also periodically transmit an indication of its presence to allow external device to detect the IPG.

At time t1, bar magnet 90 is placed over (or proximate to) the IPG. The magnetic field sensor 40 in the IPG detects the magnetic field produced by the bar magnet 90, and provides information to the mode logic 102a or 102b that a magnetic field is present. The mode logic monitors the output of the sensor 40 to determine whether a magnetic field is consistently detected for a time period, such as 2 seconds or more. Requiring the presence of a continuous magnetic field for a time period is preferred to ensure that the IPG isn't inadvertently placed into the pairing mode by a transient magnetic field to which the patient might be exposed.

If the bar magnet 90 is present for the time period (e.g., 2 seconds), the mode logic 102a or 102b issues a reset at time t2. Different functions in the IPG 100 can be affected upon reset. For example, the reset may disable the stimulation circuitry 36 and thus normal stimulation is stopped. In this respect, the bar magnet 90 acts as a safety device by providing the patient a means for stopping stimulation on an emergency basis. For example, if the stimulation being provided by the IPG is proving problematic for the patient, and the patient is not able to quickly remedy the situation using their external device, the bar magnet 90 provides a quick and safe means of easily stopping stimulation. In this regard, note that if the magnetic field is present and detected by the magnetic field sensor 40 for longer than the two-second time period, the mode logic 102a or 102b will hold the IPG in reset (from t2 to t3) until the bar magnet 90 is removed. Therefore, a patient experiencing problems can simply keep the bar magnet 90 continually proximate to the IPG to keep it in reset, and to prevent potentially problematic stimulation from re-occurring. (In this circumstance, the IPG patient would normally promptly make an appointment to see his clinician to attempt to rectify the problem). Use of a bar magnet 90 to cause a reset, and the actions that can occur in the IPG 100 when such a reset is issued, are discussed further in U.S. Pat. No. 8,473,070.

At time t3, the bar magnet 90 is removed from the IPG, and thus sensor 40 stops detecting its magnetic field. The mode logic 102a or 102b then, once the reset procedure is completed (which may take a few seconds) causes the IPG 100 to exit reset. Upon exiting reset, the mode logic 102a or 102b again enables normal stimulation, and as is most significant here also automatically causes the IPG to enter the pairing mode.

In the pairing mode, the IPG attempts to pair with an external device. How the IPG 10a or 10b operates during the pairing mode can be different in light of the communication technologies involved (MI v. RF) and standards that may be used with those technologies. However, it can be assumed here that the IPGs 10a and 10b generally operate similarly in the pairing mode. During the pairing mode, the IPGs 10a and 10b will periodically broadcast pairing data. If a BLE IPG 10b is used, that device will operate in the peripheral mode and its pairing data will include its advertisement data as discussed above. To save power, such pairing data may be periodically broadcast during transmission windows, such as every 0.5 seconds. In one example, the pairing data can comprise the IPG's ID code or serial number ("IPG1" or "IPG2"; memories 104a or 104b), which the external device may recognize (if stored in memories 114 or 122). The pairing data can also comprise additional data necessary for authentication, which may be necessary to allow the IPG to be paired with a previously-unknown external device. In this regard, the pairing data may depend on the type of connection to be established and the communication standard that govern that connection. For example, if Bluetooth or BLE is used, that standard will dictate the particulars of the pairing data to be broadcast by the IPG 10b. During pairing mode, the IPG 100 can still receive communications from external devices that were previously paired to the IPG, and should this occur, the pairing mode is exited at the IPG.

At time t4, it is assumed that an external device (either RC 50 or CP 60) is present (i.e., proximate to the IPG) and able to pair with the IPG. The user selects the IPG pairing mode at the GUI of the external device to scan for available IPGs, receives the broadcast pairing data, and populates the IPG (e.g., IPG1) for possible connection on the GUI. The user can then select to connect with the IPG to pair the external device with the IPG. If the pairing data includes IPG data already known to the external device, such as the IPG's ID code pairing and connection with the IPG can be simplified. If the pairing data does not include IPG data already known to the external device, additional authentication data may be required to allow the devices to pair. For example, the user may need to enter a password or PIN for the IPG in the GUI of the external device, or authentication can occur automatically through the exchange of secure keys at part of an authentication procedure. Again, the particulars of the pairing data and the data exchanged to allow the external device to connect to a new IPG may differ depending on the communication standard used, which can vary in different implementations.

It is preferred that the IPG not operate in the pairing mode indefinitely. In this regard, a pairing mode duration may be set and stored with the IPG's control circuitry 38a or 38b and/or mode logic 102a or 102b. This pairing mode duration is preferably long enough to give the user of the external device time to complete the pairing procedure using the RC's GUI as just explained. In one example, the pairing mode duration may be about 2 minutes. After expiration of the pairing mode duration, the mode logic 102a or 102b preferably cusses the IPG to revert to operation in its normal mode. Details concerning this pairing mode duration are omitted from the Figures for simplicity.

Once the IPG and the external device are paired and connected at time t4, the mode logic 102a or 102b in the IPG's control circuitry 38a or 38b can cause the IPG exit the pairing mode, and to automatically enter the normal mode. Normal stimulation started at t3 thus can continue, and normal telemetry can be enabled with the now-paired external device. Although not shown, both the IPG and the external device can store information relevant to the device with which its now paired, e.g., by storing relevant information about the other device in memories 106a, 106b, 114, or 122 (FIG. 3), and this may be especially useful to do if this is the first time that the IPG and external device are being paired.

Normally, and regardless of the type of IPG 10a or 10b that the patient has, pairing of the IPG 10a or 10b to the patient's RC 50 is relatively straight forward. As just explained, the patient can use the bar magnet 90 to place the IPG 10a or 10b into the pairing mode, and the RC 50 can connect with either of these types of IPGs because the RC 50 has both types of antennas (MI antenna 54a and RF antenna 54b). Other pairing mechanisms not involving use of a bar magnet 90 can also be used to pair the RC 50 with the IPG 10a or 10b.

However, difficulties involved in pairing the patient's IPG to a CP 60 are of greater concern to the inventors. When a patient presents to a clinician's office, for IPG re-programming for example, the IPG will need to be paired to the CP 60 to allow for clinician control of the IPG. But neither the patient nor the clinician may know the type of IPG that is implanted in the patient. This can cause confusion and guesswork. For example, if the patient has an MI IPG 10a with a MI coil antenna 34a, the wand 66 will need to be connected to the CP 60 and placed proximate to the patient's IPG 10a (FIG. 5C). If the patient has an RF IPG 10b with an RF antenna 34b, the wand 66 is unnecessary (FIG. 5D). The clinician might have to try pairing using both of the CP's antennas (the MI antenna 70a in the wand 66, and the RF antenna 70b in the computing device 62) before successful pairing can be established.

Further, even if the type of IPG is known, pairing with the CP 60 as described earlier can may not be optimal, particularly when a bar magnet 90 is used as part of the pairing procedure. As described earlier with respect to FIG. 5, the bar magnet 90 can be used to enable the pairing mode in the IPG, but may also cause the IPG to reset. Resetting the IPG can cause stimulation therapy to stop (t2, FIG. 5), and thus the pairing process can deprive the patient of stimulation therapy. This is particularly problematic for DBS patients, as even a brief cessation of stimulation therapy can cause their symptoms (e.g., tremor) to quickly return.

Still further, the inventors consider the use of a wand 66 with the CP 60 to be undesirable. The wand 66 as noted earlier is used for communications when the IPG includes a magnetic-induction coil antenna 34a, as in IPG 10a (FIG. 4C). The wand 66 comprises an additional device in the communication system which is expensive to make and can be cumbersome for the clinician to use. Further, the inventors believe that the IMD industry will move away from the use of magnetic inductive telemetry (IPG 10a) and towards the use of RF telemetry (IPG 10b), thus making use of the wand 66 less important in the future. Nevertheless, MI IPGs 10a will continue to exist in the patient population for some time as this market transition occurs, and the CP 60 must therefore still be able to communicate with such legacy devices. It would be preferred if CP 60 could communicate with both legacy MI IPGs 10a and more-modern RF IPGs 10b without use of wand 66.

In furtherance of these goals, the inventors disclose a communication system programmed to allow a CP 60 to communicate with MI IPGs 10a or RF IPGs 10b without the use of wand 66, even when the type of IPG is not known to the clinician or patient. Communications between the CP and the IPG are facilitated by use of the RC 50. The RC 50 is assumed to be paired to the IPG in question, and thus the RC 50 understands (even if the clinician does not) the type of IPG present in the patient by virtue of the antenna used to communicate with the paired IPG. For example, if the RC 50 is using its MI antenna 54a to communicate with the IPG, the RC 50 understands that the IPG is an MI IPG 10a; if RC 50 is using RF antenna 54b to communicate with the IPG, the RC will understand that the IPG is a RF IPG 10b.

When it is desired to connect the CP 60 for communication with an IPG, the clinician can select a CP pairing mode at the RC 50 (with the RC 50 acting in a central role). Subsequent actions taken by the RC 50 and in the system will vary depending on the RC 50's understanding of the IPG type to which it is paired.

If the RC 50 understands itself to be paired with a RF IPG 10*b*, selection of the CP pairing mode will place the IPG 10*b* into the pairing mode (in a peripheral role), and so the IPG 10*b* will begin advertising its presence. The RC 50 can disconnect from the IPG 10*b* when the IPG 10*b* enters the pairing mode. The CP 60 (in a central role) can now scan for and to connect with IPG 10*b* directly via its RF antenna 70*b*.

By contrast, if the RC 50 understands itself to be paired with a MI IPG 10*a*, selection of the CP pairing mode will cause the RC 50 to reconfigure itself in a peripheral role. Thus, the RC 50 will start advertising its presence (at RF antenna 54*b*), while still remaining paired with the IPG 10*a* (via MI antenna 54*a*). The CP 60 (in a central role) can now scan for and to connect with RC 50 (and the IPG 10*a* to which it is paired) via its RF antenna 70*b*. In effect, the RC 50 is now paired both to the CP 60 via its RF antenna 54*b* and to the IPG 10*a* via its MI antenna 54*a*. Once this occurs, the RC 50 can place itself in a passthrough mode, in which the RC 50's control circuitry 58 will pass any communications received from the CP 60 at antenna 54*b* to the IPG 10*a* via antenna 54*a*, and vice versa. The control circuit 58 when operating in the passthrough mode can reformat the data as necessary given the differences in the communication schemes used with its antennas 54*a* and 54*b* (e.g., FSK v. BLE). As such, the CP 60 is able to communicate with the IPG 10*a* using the RC 50 as a passthrough device.

This provides a seamless process for the clinician, who only needs to set the RC 50 into the CP pairing mode, and to use the GUI at the CP 60 to then connect with either the IPG 10*b* directly or to the RC 50 already paired with IPG 10*a*. Further, use of the wand 66 is unnecessary in the system and can be dispensed with.

FIGS. 6A-6E illustrate use of the CP pairing mode in the RC 50 to pair the CP 60 with a RF IPG 10*b*. In this example, communication between the devices is RF in nature (e.g., BLE), and thus antennas 34*b*, 54*b*, and 70*b* are used in the IPG 10*b*, RC 50, and CP 60.

It is assumed at time t4 that the RC 50 is paired with the IPG 10*b* using their RF antennas 54*b* and 34*b*, as described earlier with respect to FIG. 5. Note that the RC 50 understands that it is paired with a RF IPG 10*b* because it would currently be using its RF antenna 54*b* to communicate with RF IPG 10*b*. The control circuitry 58 in the RC 50 can record this fact in memory 116 (FIG. 3) as described earlier. At this point, the IPG 10*b* is in its normal mode, is providing stimulation, and telemetry is enabled with paired RC 50. The RC 50 operates in a central role, as described earlier.

At time t5, the clinician can select the CP pairing mode using the GUI of the RC 50. This can occur in different ways, as shown in FIG. 6B. At the left, the clinician has selected a pairing menu, which provides the CP pairing mode as a selectable option. At the right, the RC's lock screen is shown. As one skilled in the art will understand, the RC 50 can enter a power down mode after the RC 50 is inactive for a period. When a button is pressed on the RC, the lock screen is displayed, and the user can select unlock button 53 to activate the device. Alternatively, and relevant here, the user can press programming button 55 when the lock screen is displayed to enter the CP pairing mode. These are just examples, and the RC 50 can be placed into the CP pairing mode in different manners using the RC's GUI.

At this point, the RC 50 can determine the type of IPG to which it is currently paired. As noted earlier, this can occur by checking the contents of memory 116 (FIG. 3). Here it is assumed that the RC 50 has determined that it is connected to an RF IPG 10*b*, which causes the CP pairing mode to operate differently (compare FIGS. 7A-7E described later).

Referring again to FIG. 6A, the RC 50 transmits a CP pairing mode command 130 to the IPG 10*b*. This command places the IPG 10*b* into peripheral role if necessary (the IPG 10*b* may already be operating in a peripheral role). In further response to the CP pairing mode command 130, the IPG 10*b* sends an CP mode acknowledgment (ACK) 132 to the RC 50.

Thereafter, IPG 10*b* enters its paring mode, which can occur as described earlier by periodically broadcasting pairing data 134 during transmission windows. Notice that the IPG 10*b*'s magnetic field sensor 40 is not implicated, and thus, preferably, the IPG 10*b* does not reset (compare FIG. 5) and stimulation continues. In response to receiving the CP mode ACK 132, the RC 50 can disconnect from the IPG 10*b*. The RC 50's GUI preferably displays a message on the screen to notify the clinician that the IPG 10*b* (IPG2) has now been placed in paring mode and is available for connection at the CP 60, as shown in FIG. 6C.

Referring again to FIG. 6A, at time t6 it is assumed that the CP 60 has been brought proximate to the IPG 10*b*, which is continuing to broadcast its paring data 134 from RF antenna 34*b*. The user can now enter an option at the CP's GUI to scan for devices, as shown in FIG. 6D. Once the CP 60 receives the pairing data 134 at its RF antenna 70*b* and populates IPG 10*b* (IPG2) as a connectable device, the user can select to connect with this device, which causes the CP 60 to transmit a connection request 136 to the IPG 10*b*. At this point, the CP 60 and IPG 10*b* can try to pair. As discussed earlier, the details of such pairing may depend on the communication standard or scheme used (e.g., BLE), and additional authentication may be required, particularly if CP 60 and IPG 10*b* have not previously paired.

Once the CP 60 and IPG 10*b* are paired, the IPG 10*b* can exit the pairing mode and automatically enters the normal mode, including enabling telemetry with the now-paired CP 60. The CP 60 can at this point display information about the connection with the IPG 10*b*, as shown in FIG. 6E. This information can include the type of connection established (e.g., RF or BLE), as well as an indication of the strength of the signal (e.g., number of bars) as reported from the CP 60's of IPG 10*b*'s BLE chip set. The clinician can now use the CP 60 to program, and to receive information from, the patient's IPG 10*b*. Notice that stimulation has continued unabated, and the CP's wand 66 is not used.

FIGS. 7A-7E illustrate use of the CP pairing mode in the RC 50 to pair the CP 60 with a MI IPG 10*a*. In this example, communication between the RC 50 and the IPG 10*a* is magnetic-inductive in nature (e.g., FSK), and thus antennas 54*a* and 34*a* are used when these devices communicate. By contrast, communication between the RC 50 and the CP 60 is RF in nature (e.g., BLE), and thus antennas 54*b* and 70*b* are used when these devices communicate. Because MI communications are used between the RC 50 and the IPG 10*a*, note that the RC 50 should remain relatively close to the patient (e.g., 18 or less).

It is again assumed at time t4 that the RC 50 is paired with the IPG 10*a* using their MI antennas 54*a* and 34*a*, as described earlier with respect to FIG. 5. Note that the RC 50 understands that it is paired with a MI IPG 10*a* because it would currently be using its MI antenna 54*a* to communicate with MI IPG 10*a*. Again, the control circuitry 58 in the RC 50 can record this fact in memory 116 (FIG. 3). At this point, the IPG 10*a* is in its normal mode, is providing stimulation, and telemetry is enabled with paired RC 50. The RC 50 operates in a central role, as described earlier. As concerns magnetic induction communications, the RC 50 acts in a master role, with IPG 10*a* as the slave.

At time t7, the clinician can select the CP pairing mode using the GUI of the RC 50. This can occur in different ways, as already discussed with reference to FIG. 6B. At this point, the RC 50 can determine the type of IPG to which it is currently paired. As noted earlier, this can occur by checking the contents of memory 116 (FIG. 3). Here it is assumed that the RC 50 has determined that it is connected to an MI IPG 10*a*, which causes the CP pairing mode to operate differently than described earlier (FIGS. 6A-6E).

Figure 7A:
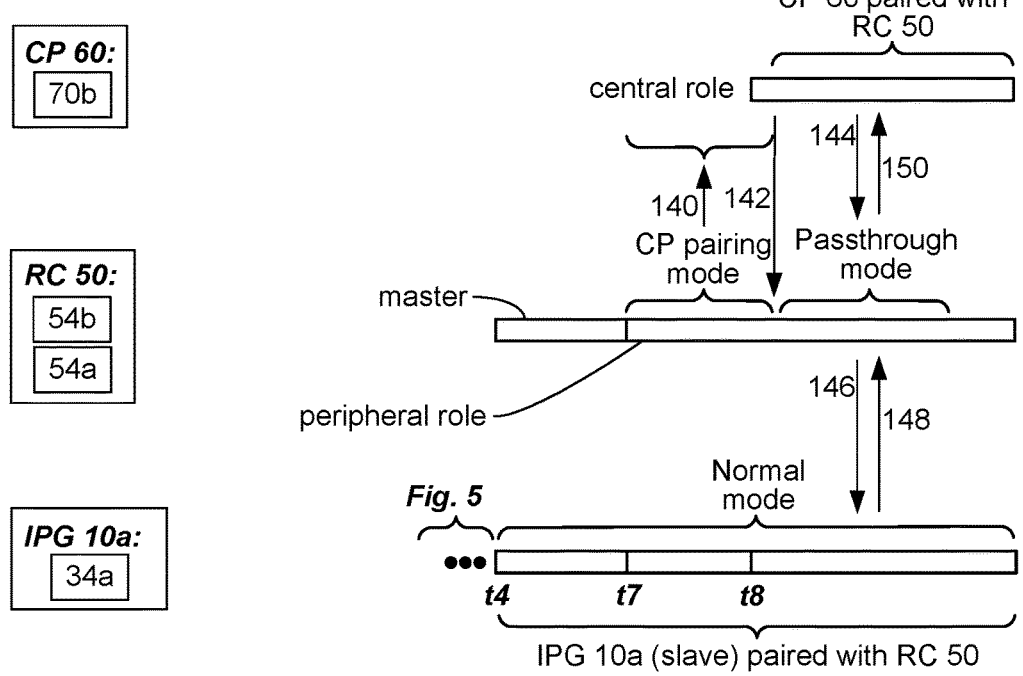
FIGS. 7A-7E show use of the RC to facilitate pairing an MI IPG to the CP, where the RC has determined that the MI IPG and CP cannot communicate directly, and hence communicate through the RC as an intermediary.
Figure 7C:
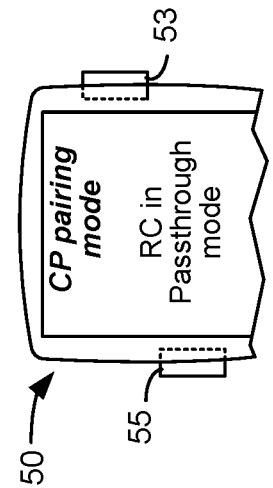
Figure 7E:
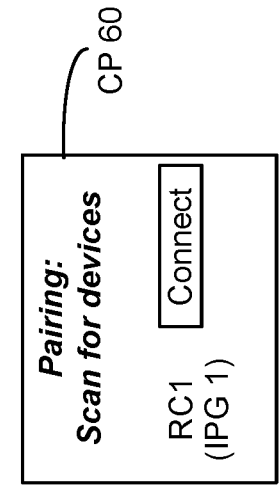
Figure 7B:
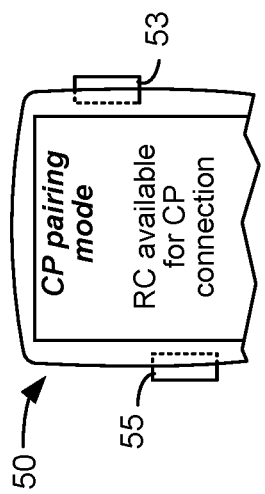

At this point, the mode logic 110 in the RC 50 can switch to operation in a peripheral role as concerns RF communications from its RF antenna 54*b*. (Note that the RC is still operating as master as concerns magnetic induction communications via MI antenna 54*a* with the IPG 10*a*). When the RC 50 enters the peripheral role, the RC 50 (not the IPG 10*a*) enters a pairing mode with the goal of eventually pairing with the CP 60. Thus, the RC 50 can periodically broadcast pairing data 140 (from RF antenna 54*b*) during transmission windows. The RC 50 may also display on its GUI that the RC 50 is now ready for connection with the CP 60, as shown in FIG. 7B.

Notice that the RC 50 and IPG 10*a* are still paired via an MI communication link established between MI antennas 54*a* and 34*a*. As such, the IPG 10*a* continues to operate in the normal mode, and MI telemetry (FSK) continues to be enabled with the paired RC 50. Further, the IPG 10*a* is not reset, and thus stimulation continues.

Referring again to FIG. 7A, at time t8 it is assumed that the CP 60 has been brought proximate to the RC 50, which is continuing to broadcast its paring data 140 from RF antenna 54*b*. The user can now enter an option at the CP's GUI to scan for devices, as shown in FIG. 7C. Once the CP 60 receives the pairing data 140 at its RF antenna 70*b*, it can populate RC 50 as a connectable device (e.g., by displaying its ID code RC1). Note that the pairing data 140 can include the RC 50's ID code and optionally may also include the IPG 10*a*'s ID code (IPG1) (which is known to the RC, because IPG 10*a* is currently paired by magnetic induction). It is useful to additionally provide the IPG's ID code as part of pairing data 140, because this can make the connection options easier to understand in FIG. 7C. For example, by displaying the connectable device as "RC1 (IPG1)" as shown in FIG. 7C, the clinician can understand that while the CP 60 will technically pair with the RC 50 (RC1), such as pairing will allow the CP 60 to communicate with the IPG 10*a* (IPG1). In other words, the clinician can understand for all intents and purposes that the CP 60 can effectively pair with the IPG 10*a*, albeit indirectly via the RC 50. At this point, the user can select to connect with RC 50 (IPG 10*a*), which causes the CP 60 to transmit a connection request 142 to the RC 50.

Figure 7D:
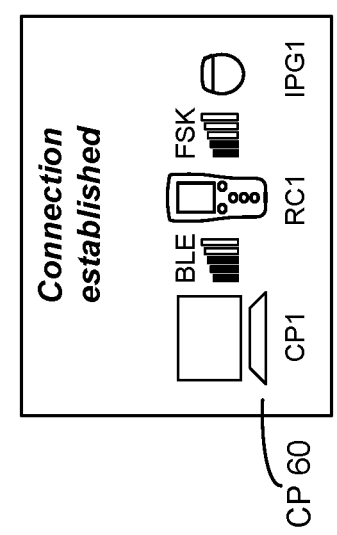

At this point, the CP 60 and RC 50 can try to pair, and as noted earlier the details of such pairing may depend on the communication standard or scheme used (e.g., BLE) and may differ in the authentication that is required. Once the CP 60 and RC 50 are paired, the CP 60 can at this display information about the connection with the RC 50 and (optionally) the IPG 10*a*, as shown in FIG. 7D. This information can include the type of connections established (e.g., BLE and FSK), as well as an indication of the strength of the signals (e.g., number of bars). Note that information about the strength of signal of the MI connection between the RC 50 and the IPG 10*a* can be determined at the RC's control circuitry 58 of the IPG 10*a*'s control circuitry 38*a*, and transmitted to the now-paired CP 60.

Once the CP 60 and RC 50 are paired, the RC 50 can exit the CP pairing mode, and, under control of its mode logic 110, preferably automatically enters a passthrough mode. When operating in the passthrough mode, the RC 50's control circuitry 58 is programmed to retransmit any RF data 144 received from CP 60 at RF antenna 54*b* as MI data 146 from MI antenna 54*a*. Similarly, the RC 50's control circuitry 58 will retransmit any MI data 148 received from IPG 10*a* at MI antenna 54*a* as RF data 150 from RF antenna 54*b*. Note that when operating in the passthrough mode that the control circuitry 58 may need to reformat data it receives (e.g., from a BLE format to a FSK or format, or vice versa) before retransmission. Essentially then, when operating in the passthrough mode, the RC 50 simply acts as a repeater to pass data between the CP 60 and the IPG 10*a*, reformatting the data as necessary. Note that the GUI of the RC 50 can reflect when it is operating in the passthrough mode, as shown in FIG. 7E. Preferably, the GUI of the RC 50 is inactive when operating in the passthrough mode, and cannot accept user inputs.

The clinician can now use the CP 60 to program, and to receive information from, the patient's IPG 10*a* via the RC as an intermediary. Notice that the IPG 10*a* operates in its normal mode through the process described in FIG. 7A, and continues to be paired with the RC 50 via magnetic induction. As such, stimulation continues unabated, and the IPG is not reset. Further, notice that the CP's wand 66 is not used, and communications with the IPG 10*a* are enabled even though the IPG 10*a* communicates by magnetic induction which is otherwise incompatible with the CP's RF antenna 70*b*.

FIG. 8 provides a summary of the disclosed technique to pair the CP to an IPG of an unknown type. At step 200, the RC 50 is paired to the IPG. This can occur using the process of FIG. 5, or any other pairing process. At step 202, the user (clinician) wishing to use her CP 60 to communicate with the IPG places the CP 50 into the "CP pairing mode" at the RC 50. As noted earlier (e.g., FIG. 6B), this can occur in different manners. At step 204, the RC 50 determines the type of IPG 10 to which is paired, e.g., whether the IPG is an MI IPG like IPG 10*a* or a RF IPG like IPG 10*b*. As noted earlier, this can involve checking the contents of memory 116 in the RC 50.

If the RC 50 determines the IPG to be of an RF type, e.g., IPG 10*b*, which is able to communicate directly with the CP 60, the RC 50 then sends a CP pairing mode command 130 to the IPG 10*b* at step 206. In step 208, the RC 50 waits for the IPG 10*b* to transmit a CP mode ACK 132, and the RC disconnects from the IPG 10*b*, and preferably displays a message that the IPG 10*b* is ready for connection to the CP 60 (FIG. 6C). The IPG 10*b* starts broadcasting its paring data 134. The CP 60 receives the pairing data 134 at step 210, and transmits a connection request 136 to the IPG 10*b*. This causes the CP 60 and IPG 10*b* to pair at step 212, thus allowing these devices to communicate using the RF communication scheme governing their connection, such as BLE. With the CP 60 now paired with IPG 10*b*, the clinician may now use the CP's GUI to transmit an operational program such as a stimulation program for the IPG 10*b*, or to transmit an adjustment to an operational program for the IPG 10*b* (e.g., to adjust one or more of its stimulation parameters, such as amplitude, pulse width, or frequency). Alternatively or additionally, the clinician may now use the CP's GUI to transmit updates for the IPG 10*b*, to receive information indicative of the status of the IPG 10*b*, or otherwise to communicate with the IPG 10*b* to any useful end.

If at step 204 the RC 50 determines the IPG to be of an MI type, e.g., IPG 10*a*, which is not able to communicate directly with the CP 60, the RC 50 at step 214 switches to a peripheral role, and begins broadcasting its pairing data 140 to the RC 50 via a RF communication link (from antenna 54*b*). The RC 50 is still paired to the IPG 10*a* by its magnetic communication link (from antenna 54*a*). The CP 60 (in a central role) receives the pairing data 140 at step 216, and sends a connection request 142 to the RC 50. This causes the CP 60 and RC 50 to pair at step 218, thus allowing these devices to communicate using the RF communication scheme governing their connection, such as BLE. After pairing, the RC 50 at step 220 enters a passthrough mode (FIG. 7E), which as described earlier reformats and retransmits received data between the MI and RF communication links. Again, with the CP 60 now paired (indirectly) with IPG 10*b*, the clinician may now use the CP's GUI to transmit an operational program or adjustments to the IPG 10*a*, to transmit updates, to receive status information, etc.

To this point it has been assumed that the CP pairing mode is used at the RC 50 when the RC 50 is paired or linked for communications with an IPG 10*a* or 10*b*. However, this is not strictly necessary, and the CP pairing mode can also be used to locate IPGs to which the CP 60 can connect. This is shown starting with FIG. 9A. Upon selecting the CP pairing mode at the RC 50 (300), the RC 50 can determine whether it is currently paired to an IPG (302). If so (303), the process can move to step 204 in FIG. 8, which as described above determines the type of IPG connected to the RC 50, and then connects the CP 60 with the IPG in accordance with the determined type.

If the RC 50 is not currently paired to an IPG (302), then the RC 50 can pair with the CP 60 in steps 310-314, similarly to what occurred in steps 214-218 in FIG. 8. At this point, the CP 60 can instruct the RC 50 to scan for MI IPGs 10*a* using its MI antenna 54*a* (315), which the RC 50 does in step 304. At step 306, the RC 50 determines whether any MI IPGs 10*a* have been located, and reports located MI IPGs 10*a*, if any, to the CP 60 via the RF communication link established (308). The CP 60 receives this information (316), and assesses whether an MI IPGs 10*a* has been located (318).

Figure 9A:
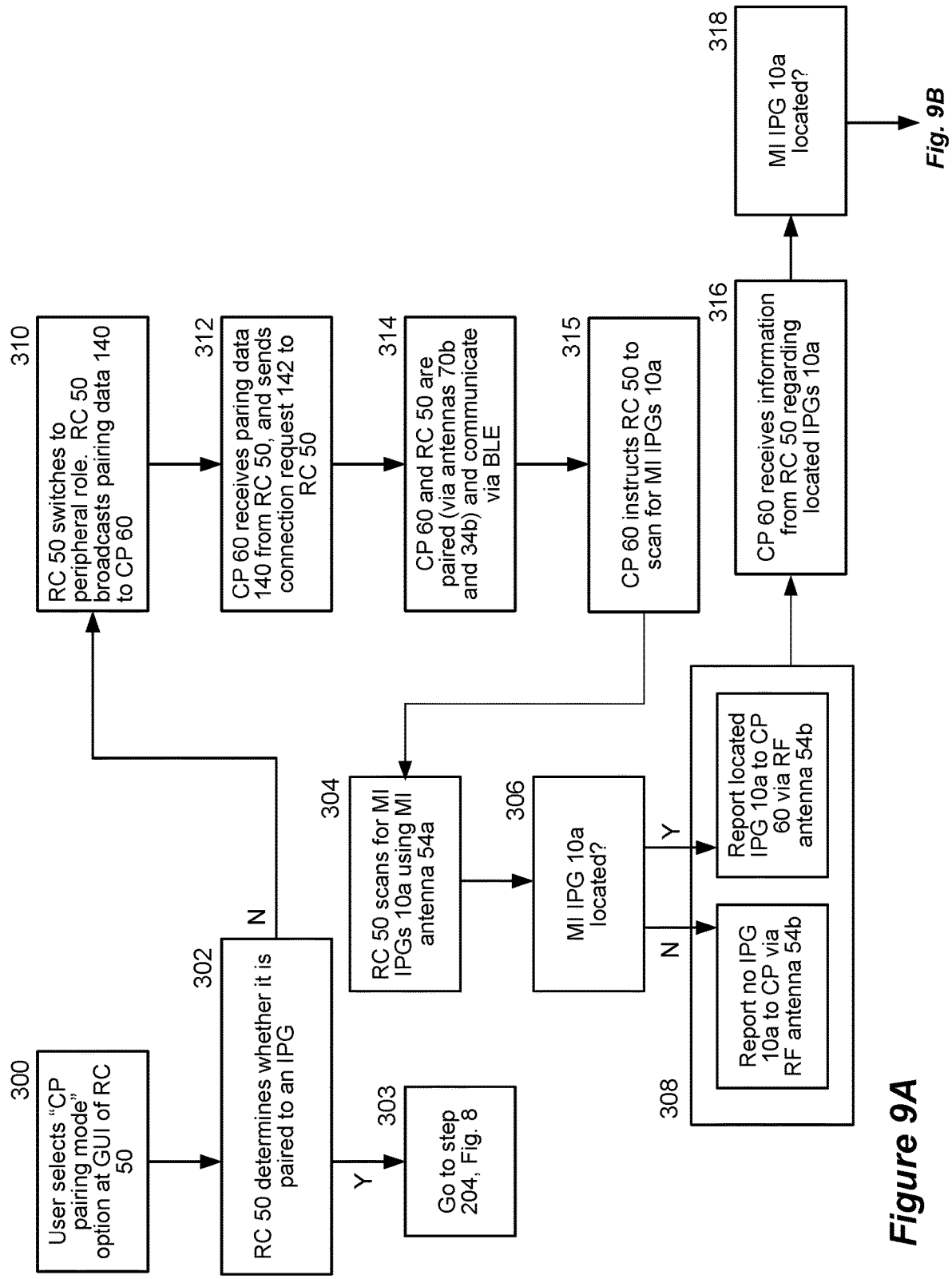
FIGS. 9A, 9B, and 10A show operation of the CP pairing mode when no IPG is initially connected to the RC.
Figure 9B:
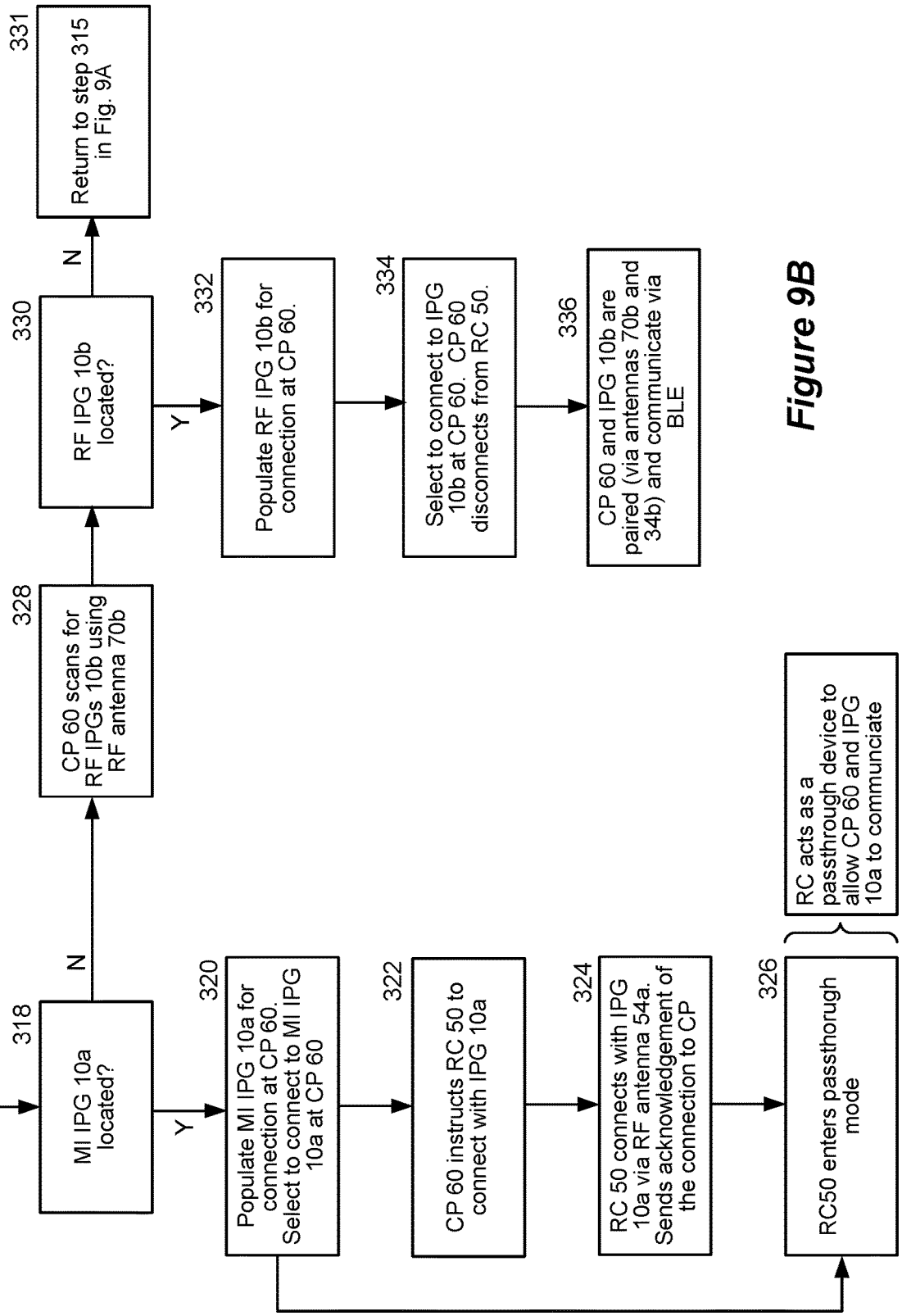
Figure 10A:
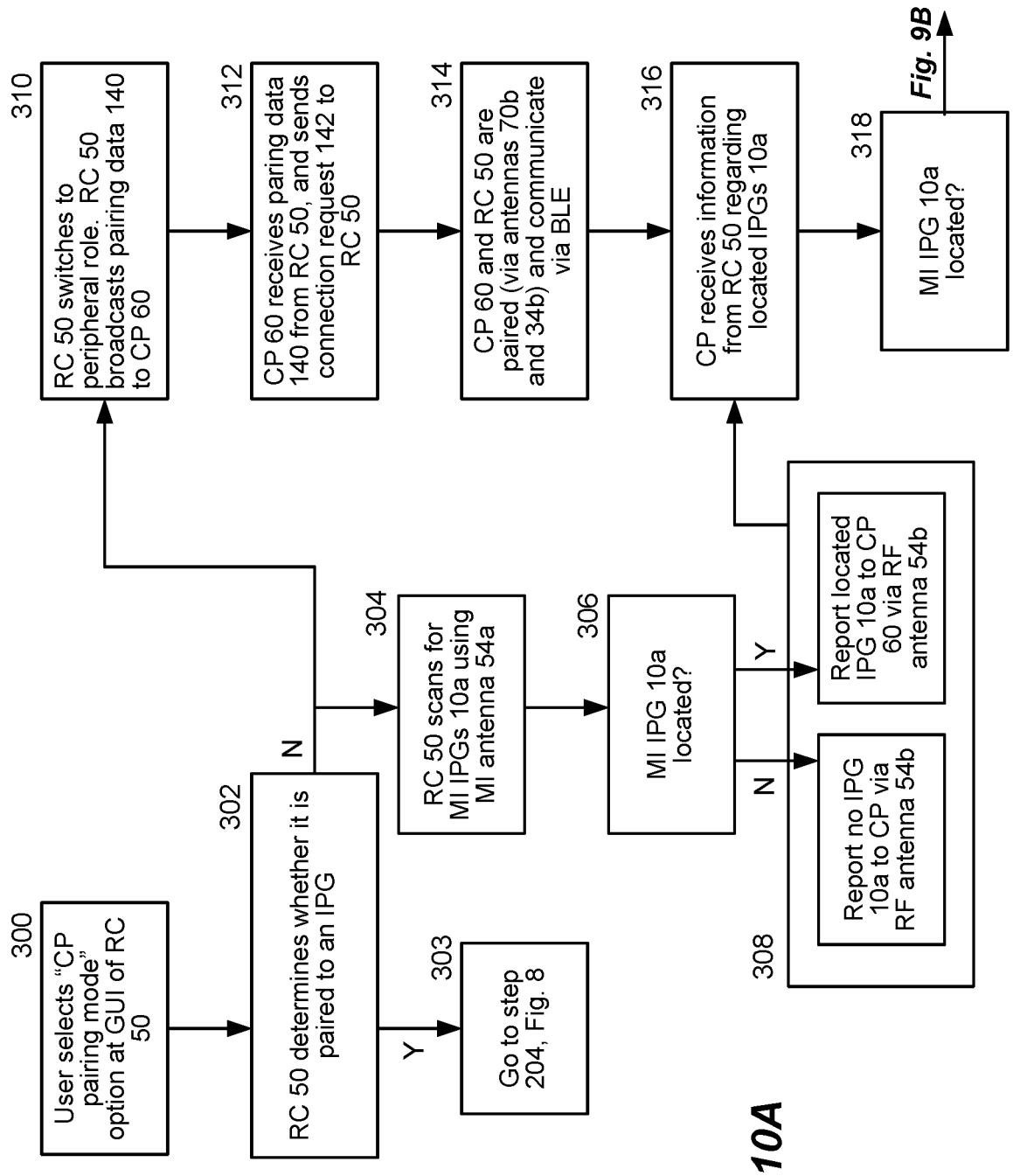

Subsequent steps are shown in FIG. 9B, but before reviewing those steps, brief reference is made to FIG. 10A. FIG. 10A shows a different manner in which the steps of FIG. 9A can be performed, and advantageously performs some of the steps in parallel. When the RC 50 determines that it is not paired to an IPG (302), the RC automatically starts scanning for MI IPGs 10*a* (304) via its MI antenna 54*a*, and in parallel starts the pairing process with the CP 60 via its RF antenna 54*b* (310-314). Once located MI IPGs have been determined (308), they are then reported to the CP 60 via the RF communication link (316). Thus, FIG. 10A differs From FIG. 9A in that the CP 60 doesn't expressly instruct the RC 50 to scan for MI IPGs 10*a*; instead, the RC 50 does this automatically at step 304. Parallel processing in FIG. 10A can make operation of the CP pairing mode quicker than in FIG. 9A.

Regardless whether the steps of FIG. 9A or FIG. 10A is used, the CP 60 determines whether the RC 50 has located any MI IPGs 10*a* (318), as shown at the top of FIG. 9B. If so, the CP 60 can populate that MI IPG 10*a* at its GUI, and a user may select to connect to it (320). At this point, the CP 60 can instruct the RC 50 to formally connect to the located MI IPG 10*a* via its MI antenna 54*a* (322). Once the RC 50 and MI IPG 10*a* have been connected, the RC 50 can send an acknowledgment of the connection to the CP (324).

Thereafter, the RC 50 can enter its passthrough mode as previously described to allow the CP 60 to communicate with the MI IPG 10*a* via the RC. Note that steps 322 and 324 may be optional: once the RC 50 has located and therefore can communicate with the MI IPG 10*a*, it may not be necessary for the CP 60 to instruct connection between the RC 50 and MI IPG 10*a* (322), or for the RC 50 to acknowledge that connection to the CP 60 (324). Instead, the RC 50 may enter the passthrough mode (326) to allow CP to IPG communications.

If no MI IPGS 10*a* were located (318), there may still be RF IPGs 10*b* with which the CP 60 can communicate, even if such IPG 10*b* are not presently known to or paired to the RC 50. In this regard, the CP 60 can scan for RF IPGs 10*b* using its RF antenna 70*b* (330). If no RF IPGs are located, the CP pairing process can end, or operation can iteratively return to step 315 in FIG. 9A, with the CP 60 again instructing the RC 50 to scan for MI IPGs 10*a* (331). If the CP 50 does locate an RF IPG 10*b* (330), that IPG 10*b* can be populated for connection at the CP's GUI (332). The user can then select to connect to this IPG 10*b* and the CP 60 can submit a connection request 136 to the RF IPG 10*b* in question (334). Because the CP 60 may only be able to connect via RF to one device at a time, the CP 60 may also disconnect from the RC 50 at this time (334). Upon receiving the connection request 136, the RF IPG 10*b* and CP are now paired, with the CP 60 able to send instructions or data to the IPG 10*b* directly.

It should be noted that application of the CP pairing mode as described does not necessarily require the use of RF and MI communication formats or standard. Instead, the technique may be applied to any different types of communications that may be used at the CP 60 and the IPG, including different RF and/or MI communication types. Furthermore, when in passthrough mode, the RC 50 need not necessary pass communication in different formats. For example, when in passthrough mode the RC can pass BLE communications from one device (e.g., the CP 60) as BLE communications to the other device (the IPG).

Furthermore, notice that the RC 50 can be used to scan for other RF IPGs 10*b* even if it is paired to the CP 60, and even if its paired to a MI IPG 10*a* via its RF antenna 54*a*. This is useful to provide different means of populating possible RF IPGs 10*b* for connection at the CP 60, and as such the CP pairing mode can be used to provide possible connections to more than one IPG. This may be especially useful should a patient have two IPGs that the CP 60 must control.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method for pairing a second external device for communications with an implantable medical device (IMD) using a first external device, the method comprising:
   (a) receiving at the first external device a first input to pair the second external device for communications with the IMD;
   (b) in response to the first input, transmitting from the first external device to the IMD a first command along a first communication link, wherein the first command causes the IMD to enter a pairing mode whereby the IMD broadcasts pairing data;
(c) receiving the pairing data at the second external device from the IMD; and
(d) receiving at the second external device a second input, wherein the second input causes the second external device to pair for communications with the IMD along a second communication link.

2. The method of claim 1, wherein the first external device is paired for communications with the IMD prior to step (a).

3. The method of claim 1, wherein step (b) further comprises receiving at the external device from the IMD an acknowledgment to the first command.

4. The method of claim 3, wherein the first external device disconnects the first communication link in response to receiving the acknowledgment.

5. The method of claim 4, wherein the first external device, upon disconnecting communication with the IMD, displays a message informing a user that the second external device can pair for communications with the IMD.

6. The method of claim 1, further comprising (e) transmitting from the second external device an operational program for the IMD or an adjustment to an operational program for the IMD along the second communication link.

7. The method of claim 1, wherein in step (d) the second input causes a second command to be transmitted from the second external device to the 1 MB.

8. The method of claim 1, wherein communications along the first and second communication links occurs using a same communication standard.

9. The method of claim 8, wherein the same communication standard comprises Bluetooth or Bluetooth Low Energy.

10. The method of claim 1, wherein the IMD comprises an implantable stimulation device (ISD) configured to provide stimulation to a patient.

11. The method of claim 10, wherein the ISD is enabled to provide the stimulation continually to the patient throughout the method.

12. The method of claim 1, further comprising after step (d) displaying an indication on the second external device that the second external device is paired for communications with the IMD along the second communication link.

13. The method of claim 12, wherein the indication indicates a strength of communications along the second communication link.

14. The method of claim 1, wherein step (b) further comprises, in response to the first input, determining in the first external device that the 1 MB is able to communicate directly with the second external device, and then transmitting the first command.

15. The method of claim 1, wherein the first external device comprises a patient remote controller, and wherein the second external device comprises a clinician programmer.

16. An implantable medical device system, comprising:
an implantable medical device (IMD);
a first external device; and
a second external device,
wherein the first external device is configured to receive a first input to pair the second external device for communications with the IMD, and to transmit to the IMD a first command along a first communication link,
wherein the IMD is configured, in response to the first command, to enter a pairing mode whereby the IMD broadcasts pairing data, and
wherein the second external device is configured to receive the pairing data, and to receive a second input, wherein the second input causes the second external device to pair for communications with the IMD along a second communication link.

17. The system of claim 16, wherein communications along the first and second communication links occurs using a same communication standard.

18. The system of claim 17, wherein the same communication standard comprises Bluetooth or Bluetooth Low Energy.

19. The system of claim 16, wherein the IMD comprises an implantable stimulation device (ISD) configured to provide stimulation to a patient.

20. The system of claim 16, wherein the first external device comprises a patient remote controller, and wherein the second external device comprises a clinician programmer.

* * * * *